United States Patent [19]

Andrianov et al.

[11] Patent Number: 5,760,271
[45] Date of Patent: Jun. 2, 1998

[54] PRODUCTION OF POLYORGANOPHOSPHAZENES

[75] Inventors: Alexander K. Andrianov, Belmont, Mass.; Jonathan R. Sargent, Los Angeles, Calif.

[73] Assignee: Virus Research Institute, Inc., Cambridge, Mass.

[21] Appl. No.: 917,793

[22] Filed: Aug. 18, 1997

[51] Int. Cl.$^6$ .................................. C07F 9/24
[52] U.S. Cl. ........................... 558/93; 558/157
[58] Field of Search ........................ 558/93, 157

[56] References Cited

U.S. PATENT DOCUMENTS

| | | |
|---|---|---|
| 3,939,228 | 2/1976 | Kao .................................... 558/93 |
| 5,053,451 | 10/1991 | Allcock et al. . |
| 5,494,673 | 2/1996 | Andrianov et al. . |
| 5,529,777 | 6/1996 | Andrianov et al. . |

OTHER PUBLICATIONS

Andrianov, et al., *J. Appl. Pol. Sco.*, vol. 53, pp. 1573–1578 (1994).

*Primary Examiner*—Michael G. Ambrose
*Attorney, Agent, or Firm*—Elliot M. Olstein; Raymond J. Lillie

[57] ABSTRACT

A process for producing a polyorganophosphazene from a polyhalophosphazene. The polyhalophosphazene is reacted with a metal salt of an alkyl ester of hydroxybenzoic acid wherein the metal salt of the alkyl ester of hydroxybenzoic acid is contained in a homogeneous melt solution. The reaction of the polyhalophosphazene with the metal salt of an alkyl ester of hydroxybenzoic acid produces a macromolecular substituted polymer, which is reacted with a base to hydrolyze the polymer and produce the desired polyorganophosphazene product.

10 Claims, No Drawings

PRODUCTION OF POLYORGANOPHOSPHAZENES

This invention relates to the production of polyorganophosphazenes, such as, for example, poly[di (carboxylatophenoxy)phosphazene], or PCPP. More particularly, this invention relates to the production of polyorganophosphazenes from polyhalophosphazenes by reacting a polyhalophosphazene with a metal salt of an alkyl ester of hydroxybenzoic acid to effect macromolecular substitution of the polyhalophosphazene with subsequent hydrolysis of the polymer with base to form the polyorganophosphazene. In the present invention, the salt of the alkyl ester of hydroxybenzoic acid is contained in a homogenous melt solution of an alkyl ester of hydroxybenzoic acid and a metal salt of an alkyl ester of hydroxybenzoic acid.

Polyphosphazenes, such as polyorganophosphazenes including poly[di(carboxylatophenoxy)phosphazene] or PCPP, are useful as immunoadjuvants and as materials for microencapsulation, as described in U.S. Pat. Nos. 5,494, 673, issued to Andrianov, et al.; and 5,529,777, issued to Andrianov, et al. PCPP can be obtained by the macromolecular substitution of polydichlorophosphazene with sodium alkyl p-hydroxybenzoate in dioxane or tetrahydrofuran (THF) with subsequent hydrolysis of the ester group containing polymer with base to yield PCPP as described in U.S. Pat. No. 5,053,451, issued to Allcock, et al. The modification reagent, sodium alkyl p-hydroxybenzoate, however, is not soluble in dioxane, THF, or any other common solvent of choice for the modification reaction, such as benzene or toluene. This reagent usually is obtained in situ by mixing, for example, ethyl hydroxybenzoate, with sodium spheres in dioxane and heating this mixture under reflux for 10 hours (U.S. Pat. No. 5,053,451) or by reacting propyl p-hydroxybenzoate, or propyl paraben, in THF with a 60% suspension of sodium hydride in mineral oil (Andrianov, et al., *J. App. Pol. Sci.*, Vol. 53, pgs. 1573–1578 (1994)). The in situ synthesis of the reagent using reactive sodium, which is difficult to handle, increases process costs. The use of the less reactive suspension of sodium hydride in mineral oil presents the problem of the separation of oil from the contaminated product, resulting in extra process costs due to additional purification procedures. Sodium propyl paraben is available commercially, but was not used in the synthesis of PCPP because of its poor solubility in the reaction mixture.

It is an object of the present invention to provide a process for producing polyorganophosphazenes, such as PCPP, without the need for an intermediate in situ synthesis of the modification reagent. It also is another object of the present invention to reduce the contamination of the polyorganophosphazene product with materials used in or reaction by-products used in the synthesis of the modification reagent.

In accordance with an aspect of the present invention, there is provided a process for producing a polyorganophosphazene. The process comprises heating an alkyl ester of hydroxybenzoic acid to a temperature sufficient to melt the alkyl ester of hydroxybenzoic acid. A metal salt of an alkyl ester of hydroxybenzoic acid is added to the melted alkyl ester of hydroxybenzoic acid to form a homogenous melt solution of the alkyl ester of hydroxybenzoic acid and the metal salt of an alkyl ester of hydroxybenzoic acid. A solution which includes a polyhalophosphazene and an organic solvent is added to the homogeneous melt solution to form a reaction mixture. The polyhalophosphazene is reacted with the metal salt of an alkyl ester of hydroxybenzoic acid, whereby there is produced a substituted polyphosphazene. The substituted polyphosphazene then is reacted with a base to form the polyorganophosphazene.

The alkyl ester of hydroxybenzoic acid is heated to a temperature sufficient to melt the alkyl ester of hydroxybenzoic acid. In general, the alkyl ester of hydroxybenzoic acid is heated to a temperature of at least 100° C., preferably from about 100° C. to about 140° C. In one embodiment, the alkyl ester of hydroxybenzoic acid and the metal salt of an alkyl ester of hydroxybenzoic acid each have an alkyl moiety having from 1 to 6 carbon atoms. In another embodiment, the alkyl moiety is propyl.

In yet another embodiment, the metal salt of an alkyl ester of hydroxybenzoic acid is a Group I metal salt of an alkyl ester of hydroxybenzoic acid. In one embodiment, the Group I metal is sodium.

Polyhalophosphazenes which may be reacted include, but are not limited to, polychlorophosphazenes. In one embodiment, the polychlorophosphazene is polydichlorophosphazene. Other polyhalophosphazenes which may be employed include, but are not limited to, polyorganohalophosphazenes having organic side moieties, such as, for example poly[(carboxylatophenoxy) chlorophosphazene].

In one embodiment, the organic solvent in which the polyhalophosphazene is dissolved is diglyme.

In another embodiment, the base is a Group I metal hydroxide, and preferably potassium hydroxide.

Polyorganophosphazenes which may be produced in accordance with the present invention include, but are not limited to, poly[di (carboxylatophenoxy) phosphazene], or PCPP, and poly[(carboxylatophenoxy methoxy ethoxy ethoxy) phosphazene].

In a most preferred embodiment, propyl p-hydroxybenzoate, or propyl paraben, is heated to a temperature sufficient to melt the propyl paraben. The propyl paraben melt may be formed in the presence of diglyme, which may be present in an amount of up to about 25% by weight. Sodium propyl paraben then is added to the melt to form a homogenous melt solution.

A solution of polydichlorophosphazene in diglyme then is mixed with the homogeneous melt solution to form a reaction mixture, whereby macromolecular substitution of the polydichlorophosphazene is effected. Potassium hydroxide then is added to effect hydrolysis of the polymer, thereby forming poly[di(carboxylatophenoxy)phosphazene], which is precipitated from the solution. The PCPP then is isolated and recovered by any of a variety of means known to those skilled in the art.

The invention now will be described with respect to the following examples; however, the scope of the present invention is not intended to be limited thereby.

EXAMPLE 1

85 g of propyl paraben was mixed with 19.7 g of diglyme. The mixture was heated with constant stirring until all the propyl paraben melted. 96 g of sodium propyl paraben then was added to the melt and the mixture heated to dissolve the sodium propyl paraben in the melt. The obtained melt solution then was diluted with 190 ml of diglyme.

The propyl paraben solution then was added to a solution of 130 g (4.66% wt/vol.) of polydichlorophosphazene solution in diglyme with constant stirring. The reaction mixture was refluxed for 8 hours, and then cooled to 95° C. A solution of 100 g of potassium hydroxide in 111 ml of water was added slowly with vigorous stirring to the reaction mixture to bring about the hydrolysis of the substituted polymer and consequent precipitation of PCPP. 20 ml of water then was added to facilitate a good phase separation. The liquid organic layer was decanted, and the precipitate was dissolved in 1 liter of deionized water, and then reprecipitated by addition of 400 ml of saturated sodium chloride solution. The aqueous layer was decanted, and the precipitate redissolved in 150 ml of deionized water, and precipitated finally by addition of 150 ml of ethanol. The PCPP precipitate was filtered and dried. The yield of PCPP was 6.2 g (84%).

EXAMPLE 2

42.5 g of propyl paraben was heated with constant stirring until all the propyl paraben melted. 48 g of sodium propyl paraben then was added to the melt and the mixture heated to dissolve the sodium propyl paraben in the melt.

The propyl paraben solution was then added to a solution of 1.13 g (0.73% wt/vol.) of polydichlorophosphazene solution in diglyme with constant stirring. The reaction mixture was refluxed for 2 hours, and then cooled to 95° C. A solution of 50 g of potassium hydroxide in 56 ml of water was added slowly with vigorous stirring to the reaction mixture to bring about the hydrolysis of the substituted polymer and consequent precipitation of PCPP. 10 ml of water then was added to facilitate a good phase separation. The liquid organic layer was decanted, and the precipitate was dissolved in 400 ml of deionized water, and reprecipitated by the addition of 200 ml of 15% sodium chloride solution. The aqueous layer was decanted, and the precipitate redissolved in 100 ml of deionized water, and precipitated finally by the addition of 100 ml of ethanol. The PCPP precipitate was filtered and dried. The $^{31}$P NMR spectra in $D_2O$ showed a peak at −15.8 ppm which confirmed the product to be PCPP. The yield of PCPP was 1.77 g (52%).

It is to be understood, however, that the scope of the present invention is not to be limited to the specific embodiments described above. The invention may be practiced other than as particularly described and still be within the scope of the accompanying claims.

What is claimed is:

1. A process for producing a poly[di(carboxylatophenoxy) phosphazene], comprising:

(a) heating an alkyl ester of hydroxybenzoic acid to a temperature sufficient to melt said alkyl ester of hydroxybenzoic acid;

(b) adding a metal salt of an alkyl ester of hydroxybenzoic acid to said melted alkyl ester of hydroxybenzoic acid to form a homogeneous melt solution of said alkyl ester of hydroxybenzoic acid and said metal salt of an alkyl ester of hydroxybenzoic acid;

(c) mixing a solution including a polyhalophosphazene and an organic solvent with said homogeneous melt solution to form a reaction mixture and produce thereby a substituted poly[di(carboxylatophenoxy) phosphazene]; and (d) reacting said substituted poly[di(carboxylatophenoxy) phosphazene] with a base to effect hydrolysis of and to form said poly[di(carboxylatophenoxy)phosphazene].

2. The process of claim 1 wherein said polyhalophosphazene is polydichlorophosphazene.

3. The process of claim 1 wherein said organic solvent is diglyme.

4. The process of claim 1 wherein said alkyl ester of hydroxybenzoic acid and said metal salt of an alkyl ester of hydroxybenzoic acid each include an alkyl moiety having from 1 to 6 carbon atoms.

5. The process of claim 4 wherein said alkyl moiety of said alkyl ester of hydroxybenzoic acid and of said metal salt of an alkyl ester of hydroxybenzoic acid is propyl.

6. The process of claim 1 wherein said metal salt of an alkyl ester of hydroxybenzoic acid is a Group I metal salt of an alkyl ester of hydroxybenzoic acid.

7. The process of claim 1 wherein said organic solvent is diglyme.

8. The process of claim 1 wherein said base is a Group I metal hydroxide.

9. The process of claim 8 wherein said base is potassium hydroxide.

10. The process of claim 1 wherein said alkyl ester of hydroxybenzoic acid in step (a) is heated in the presence of diglyme, wherein said diglyme is present in an amount of up to about 25% by weight.

* * * * *